United States Patent [19]
Welch
[11] Patent Number: 4,809,573
[45] Date of Patent: Mar. 7, 1989

[54] ADAPTIVE TORQUE CONTROL OF CUTOFF KNIFE PULL ROLL

[75] Inventor: Harold D. Welch, Phillips, Wis.

[73] Assignee: Marquip. Inc., Phillips, Wis.

[21] Appl. No.: 113,552

[22] Filed: Oct. 26, 1987

[51] Int. Cl.[4] ........ B26D 31/00
[52] U.S. Cl. ........ 83/37; 83/71; 83/72; 83/76; 83/295; 83/298; 83/360; 83/364; 83/368; 83/370; 83/371
[58] Field of Search ........ 83/71, 72, 76, 295, 83/298, 360, 364, 368, 370, 371, 37

[56] References Cited

U.S. PATENT DOCUMENTS

| | | | |
|---|---|---|---|
| 4,283,975 | 8/1981 | Knol | 83/76 |
| 4,426,898 | 1/1984 | Friberg | 83/37 |
| 4,464,959 | 8/1984 | Larson | 83/37 |
| 4,627,214 | 12/1986 | Anderson et al. | 83/71 |
| 4,669,344 | 6/1987 | Herrig | 83/27 |
| 4,724,732 | 2/1988 | Miyauchi et al. | 83/37 |
| 4,731,733 | 3/1988 | Knoll | 83/71 X |

*Primary Examiner*—William L. Sikes
*Assistant Examiner*—Frank González
*Attorney, Agent, or Firm*—Andrus, Sceales, Starke & Sawall

[57] ABSTRACT

A control system is established wherein, when there is a flow of continuous web material (2), an identification phase is provided by increasing the torque signal to a pull roll motor (13) until slippage between the pull roll (12) and continuous web is created at a breakaway torque point, the value of which is measurable. The pull roll motor is then caused to be driven by a signal which creates a motor torque output which is of a value less than the breakaway torque point. Thus, no slippage can occur. As the motor is driven at the lower torque value, a calibration phase is entered wherein an encoder output of the pull roll is properly equated with that of a measuring wheel (9), this phase occuring at a time when there can be no slip between the web-roll interface. The identification-calibration process can be repeated as often as desired. The control system further includes the ability to cause acceleration of the pull roll after the web has been severed upstream to thereby accelerate the tail or downstream portion of the severed discontinuous web until a desired gap is created for use in a slitting device (6). At this point, which is subsequent to the identification-calibration phases, the control returns the motor input to the lower torque value.

14 Claims, 2 Drawing Sheets

ADAPTIVE TORQUE CONTROL OF CUTOFF KNIFE PULL ROLL

BACKGROUND AND SUMMARY OF THE INVENTION

This invention relates to an adaptive torque control of a cutoff knife pull roll. The invention is concerned with traveling webs of continuous sheet material, such as paperboard or the like, and concepts involving the handling thereof.

During normal operation of known web handling equipment, such as a corrugator or the like, a continuous web of sheet material is fed to a cutoff knife which severs the web transversely to form rectangular sheets of uniform length which are then fed downstream for further processing. A measuring wheel assembly is disposed upstream of the knife and includes a wheel which rides on the web, with the wheel shaft driving a position encoder which creates a signal which in turn actuates the knife for cutoff.

In some instances, it is desired to slit the traveling web longitudinally into a plurality of separate narrower side-by-side web segments. This is accomplished by a slitting machine which is disposed upstream of the cutoff knife. The slitting machine may be of the type disclosed in U.S. Pat. No. 4,627,214 issued Dec. 9, 1986, and includes a plurality of transversely spaced slitting tools which may be adjusted transversely to vary the width of the slit web segments. This adjustment can only be made when no web is present in the machine.

If it is desired to adjust the slitting tools without completely stopping the run of web, with its undesirable machine downtime, it is necessary to form a gap in the web. Previously known devices have formed such a gap by providing a shear upstream of the slitting machine and measuring wheel assembly. The shear is used to transversely sever the traveling web to form a separate downstream "tail" portion which is then accelerated relative to the web portion upstream of the sever. The resultant gap then allows transverse adjustment of the slitter tooling.

Immediately after shearing, the measuring wheel assembly is no longer effective in measuring the web for cutoff purposes because the measuring wheel is not being driven by the tail. In order to continue accurate cutoff length of the tail, measurement of the web is transferred from the measuring wheel assembly to a pull roll assembly located adjacent and just upstream of the cutoff knife. The pull roll assembly has usually consisted of a motively driven pull roll disposed beneath the web, and holddown idler roll wheels disposed above the web which biases the web downwardly against the pull roll. A position encoder is driven by the pull roll for purposes of taking over the signaling duties from the measuring wheel encoder.

In transferring the signal output from the measuring wheel encoder to the pull roll encoder after shearing, it is essential that their outputs be properly equated. In known devices, this has been accomplished by calibrating the pull roll with respect to the measuring wheel at a time when there is continuous web flow of equal velocity passing both measuring devices. A computer control has been utilized to accomplish the desired equating by applying a suitable multiplication factor to the pull roll encoder.

It is furthermore essential that, during calibration, no slipping occurs at the interface between the pull roll and the web. Heretofore, attempts have been made to eliminate slip by manually limiting the maximum torque output of the motive means, hereinafter referred to as a motor, driving the pull roll. However, problems occur in that various operating conditions may nevertheless cause slip. Such conditions may include the desire to pull a heavy web into and through the cutoff knife, and yet not slip on a very narrow web. Furthermore, the coefficient of friction between the web and pull roll can vary widely and cause slippage whenever the coefficient is low.

The concepts of the present invention are directed to assuring that the pull roll assembly does in fact accurately measure web travel after the web has been severed at the upstream shear.

In accordance with the various aspects of the invention, a control system is established wherein, when there is a flow of continuous web, an identification phase is provided by increasing the torque signal to the pull roll motor until slippage between the pull roll and continuous web is created at a breakaway torque point, the value of which is measurable. The pull roll motor is then caused to be driven by a signal which creates a motor torque output which is of a value less than the breakaway torque point. Thus, no slippage can occur. As the motor is driven at the lower torque value, a calibration phase is entered wherein the encoder output of the pull roll is properly equated with that of the measuring wheel, this phase occurring at a time when there can be no slip between the web-roll interface. The identification-calibration process can be repeated as often as desired.

The control system further includes the ability to cause acceleration of the pull roll after the web has been severed upstream to thereby accelerate the tail or downstream portion of the severed discontinuous web until the desired gap is created for use in a slitting device, as described earlier. At this point, which is subsequent to the identification-calibration phases, the control returns the motor input to the lower torque value.

BRIEF DESCRIPTION OF THE DRAWINGS

The accompanying drawings illustrate the best mode presently contemplated by the inventor for carrying out the invention.

In the drawings.

DESCRIPTION OF THE PREFERRED EMBODIMENT

Figure 1:
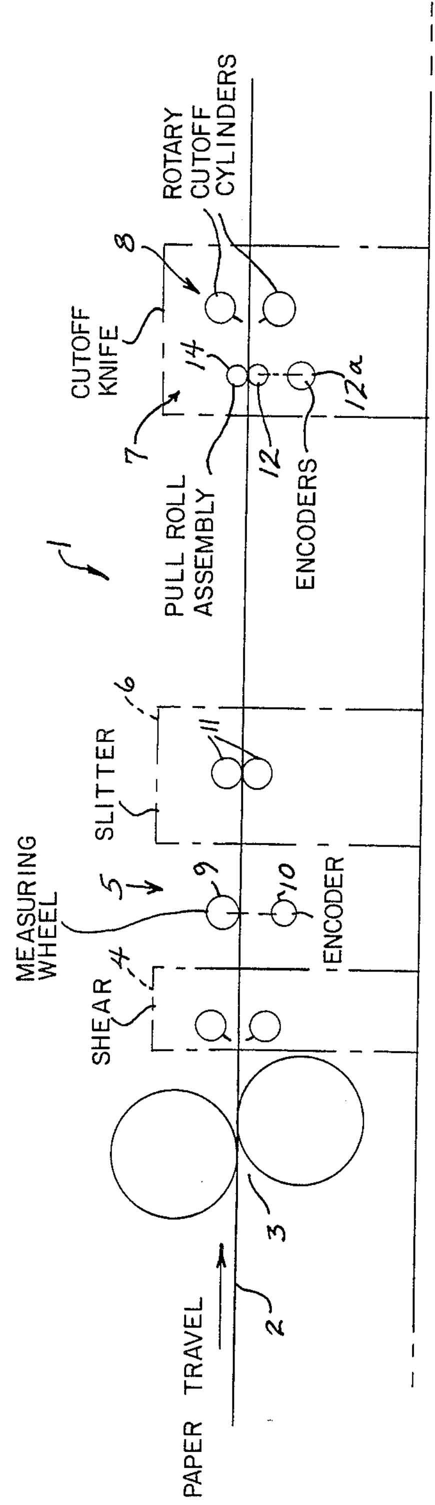
FIG. 1 is a schematic representation of a web handling device which incorporates the various aspects of the invention.
Figure 2:
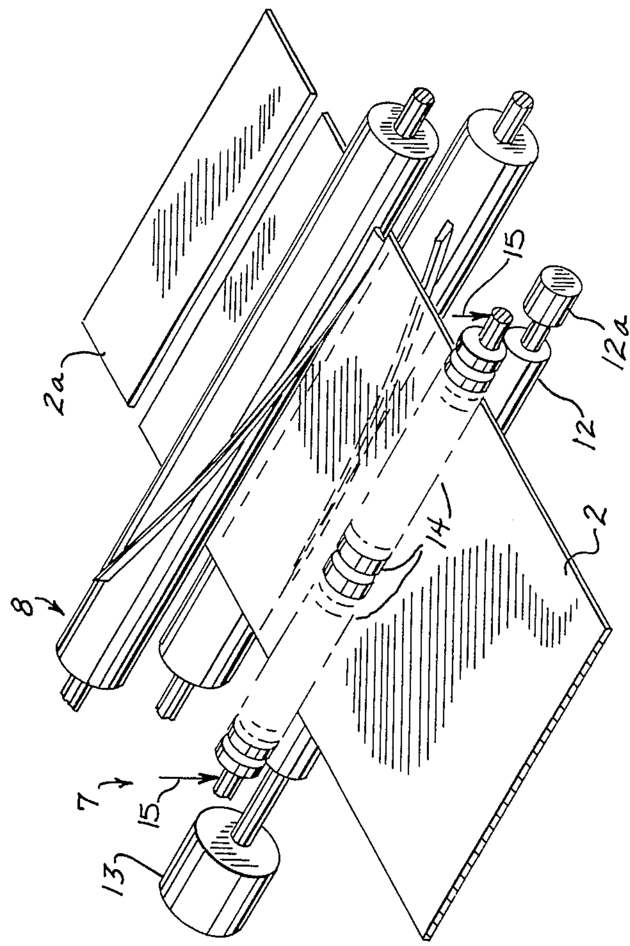
FIG. 2 is a fragmentary schematic perspective view of the cutoff knife station and pull roll assembly station.

Referring especially to FIGS. 1 and 2, a web handling apparatus 1 is adapted to process a continuous length of web 2 which travels through the apparatus from an upstream processing apparatus, not shown. Web 2 is adapted to be slit into longitudinal segments and subsequently cut transversely into sheets of equal length and then discharged downstream for further processing, such as by a stacker.

As shown, apparatus 1 generally includes (from upstream to downstream) an input nip 3, a transverse shear 4 of any suitable well-known type, a measuring wheel assembly 5, a longitudinal slitter 6, a pull roll assembly 7, and a transverse cutoff knife 8 of any suitable well-known type which is actuated in any known manner to separate web 2 into a plurality of web sheets 2a which are discharged from the machine. Measuring wheel assembly 5 includes a measuring wheel 9 which rides on the top of web 2, and a position encoder 10 on the wheel shaft which provides an output signal in accordance with a point on the web and controls cutoff knife 8. Slitter 6 is provided with a plurality of transversely positioned cutting blades 11 (only one set of which are shown) for selectively slitting web 2 longitudinally into a plurality of side-by-side segments. Wheels 11 are adjustable transversely for selectively varying the segment widths. U.S. Pat. No. 4,627,214 discloses a slitter of suitable type, and is incorporated herein by reference. Pull roll assembly 7 includes a pull roll 12 disposed beneath web 2 and driven by a motive means, such as a motor 13. A position encoder 12a is disposed on the pull roll shaft which also provides an output signal in accordance with a point on the web. A set of idler holddown wheels 14 is disposed above web 2 and are provided with any suitable biasing means illustrated by the arrows 15 to press web 2 against pull roll 12.

Figure 3:
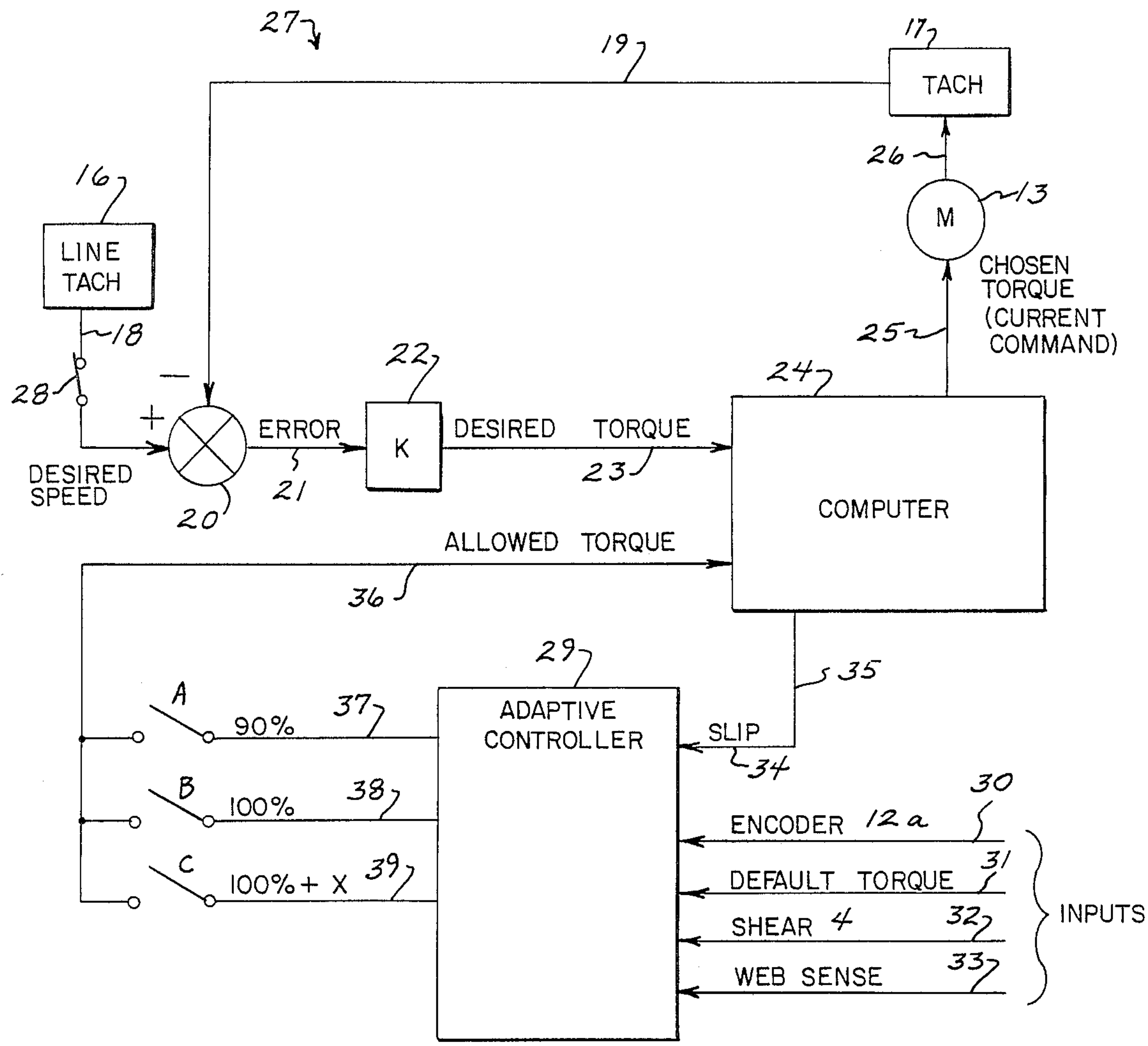
FIG. 3 is a block diagram of an embodiment of suitable control system for the device.

As best seen in FIG. 3, a pair of velocity measuring devices, such as tachometers 16 and 17, are also included in the apparatus. Tachometer 16 is a line tachometer disposed upstream of shear 4 (and may in fact be upstream of the apparatus itself), and is connected to a device riding on web 2, thus providing an output signal through a line 18 which is in accordance with the web velocity, which is the desired velocity. Tachometer 17 is disposed on pull roll assembly 7 and is connected to pull roll 12, thus providing a signal through a line 19 which is in accordance with the rotational velocity of pull roll 12.

As schematically illustrated in the upper portion of FIG. 3, the output signals of tachometers 16 and 17 are fed through lines 18 and 19 to an error set point device 20 which measures any difference in velocities of a continuous web 2 and pull roll 12. Set point device 20 is connected through a line 21 to an electronic amplifier 22 which applies an electronic factor (sometimes called a multiplication factor) to the incoming signal which is in accordance with and equates the known difference in bits so that one bit on measuring wheel assembly 5 represents the same amount of web travel as one bit on pull roll assembly 7. The output signal of amplifier 22, representing the desired torque drive signal for motor 13, is fed through a line 23 to a suitable programmable computer 24 which may be of any well-known type. Computer 24 feeds a torque drive signal through a line 25 to motor 13, which in turn is connected to tachometer 17 through a line 26 which in fact is a mechanical connection therebetween. The result is a velocity servo loop 27, which is of a known type.

If the output signals from tachometers 16 and 17 are equal, no error signal is introduced into the loop and computer 24 will provide a torque drive signal through line 25 to motor 13 in exact accordance with the incoming torque drive signal in line 23. However, in the event that pull roll 12 slips on web 2, the signals from tachometers 16 and 17 will not be equal, thus producing an error signal at set point device 20. When this is fed to computer 24, the latter will adjust its output torque drive signal to motor 13 to bring pull roll 12 back to a non-slipping equilibrium condition.

The above described operation is operative when a continuous web of sheet material is passing through web handling apparatus 1.

As previously described, it is desirable to make transverse adjustments to slitter blades 11 while the machine is running. In order to accomplish this, there must be a period when no web is passing through the slitter. For this purpose, previously known devices have used a shear, such as shear 4, to sever web 2 transversely to form a downstream tail portion and an upstream portion coming in from the upstream processing device. Under the control of a computer, such as computer 24, the downstream tail portion of the now discontinuous web is then accelerated by its drive, such as pull roll 12, to pull it away from the upstream portion to thus form a gap which passes through slitter 6, giving blades 11 time to be adjusted before the upstream web portion arrives.

As the gap is formed, measuring wheel 9 no longer is in contact with a web portion so that the signal from its position encoder 10 is unavailable to properly actuate cutoff knife 8. Thus, the previous devices were arranged to transfer the necessary web position signal from measuring wheel encoder 10 to pull roll encoder 12a. This was accomplished by calibrating the pull roll with respect to the measuring wheel during run of a continuous web and before web severing. This calibration actually takes place during operation of the servo loop 27 described above, and is under the control of computer 24 and the multiplication factor presented by amplifier 22. When calibration has been effected and the pull roll is in sync with the measuring wheel, shear 4 can be "fired" and the pull roll takes over to control cutoff knife 8.

Previous devices which operated in this manner have been subject to a problem of slippage at the interface between the pull roll and the downstream severed web "tail" portion. Such slippage has resulted in lack of uniformity of length of the sheets cut from the tail portion by the cutoff knife 8. Previous attempts to eliminate this slippage have not been successful. One such attempt has included manually setting the apparatus so that the torque output of the pull roll drive motor is at a fixed value below what would be the normal setting. Variations in web weight, segment width and the coefficient of friction at the web-pull roll interface have nevertheless still prevented the elimination of slippage.

The aspects of the present invention provide a unique concept wherein the problems associated with the prior devices are essentially eliminated.

Referring again to the schematic showing of FIG. 3, a normally closed switch 28 is disposed in output line 18 of tachometer 16, for purposes to be described. In addition, an adaptive controller 29 is provided in the control circuit. Controller 29 contains an oscillator, timing device, switch actuating circuits and other circuitry of well known type to accomplish its desired function.

Controller 29 is provided with a plurality of inputs. The "Encoder 12a" input 30 is a web position signal from the pull roll encoder. The "Default Torque" input 31 is utilized under a suitable control, such as computer 24, to get the system up and running. The "Shear 4" input 32 signals when the shear has been actuated. The "Web Sense" input 33 signals the presence or absence of a web adjacent cutoff knife 8. The controller furthermore has a so-called "slip" input 34 which is under the control of computer 24 and provides a signal through a connecting line 35 in a manner to be described. These input signals are all coordinated within the controller in any well known manner to function in accordance with the inventive concepts.

A common line 36 connects controller 29 with computer 24 and serves as the controller output which feeds an "Allowed Torque" signal to the computer. As shown, controller 29 outputs to line 36 through a plurality of lines 37, 38 and 39 which are provided with controller-controlled switches designated respectively as A, B and C. For purposes of illustration, the signals passing through lines 37–39 are designated as 90%, 100% and 100%+X, as will be described.

The aspects of the invention contemplate providing an identification phase during normal run of a continuous unsevered web 2 which identifies and measures the breakaway torque point or threshold at which motor 13 will cause slippage at the interface between the web and pull roll. This is accomplished by gradually increasing the torque which motor 13 applies to pull roll 12. When the torque exceeds the resistance applied to the roll by web 2, slippage will occur. The motor velocity will then suddenly increase or "ramp up" to a higher value with a resultant drop in motor torque. The control circuit monitors for this breakaway torque condition and causes the torque applied to the motor to drop to a value below that at which slippage will occur, and then recalibrates the measuring wheel and pull roll operations if necessary.

Assume velocity servo loop 27 is operating as described above, with switch 28 closed and switches A, B and C open. Velocity servo loop 27 is operating as described above and web 2 is traveling at its initial or desired speed. When controller 29 determines via timing or the like that an identification phase should be initiated, controller 29 closes switch B which allows a torque increasing signal to pass to computer 24 and hence to motor 13. The motor torque will continuously and gradually increase until slippage occurs between the web-pull roll interface. This is the breakaway point. The slippage will be sensed by computer 24 which passes a suitable slip signal to controller 29 via line 35. Controller 29 will then simultaneously open switch B and close switch A. Switch A allows a torque decreasing signal to pass through lines 37 and 36 to computer 24 and hence to motor 13, thus eliminating the slippage.

In the showing of FIG. 3, at the time of breakaway, controller output line 38 will be providing a torque signal through line 36 which is 100% of the breakaway torque. When switch B is opened and switch A closed, output line 37 will be caused by the controller to provide a lowered torque, indicated here as 90% by way of example only.

This ends the identification phase.

Subsequently, the machine will continue to operate with motor 13 providing the lowered non-slip torque. During this time, and with a continuous unsevered web, velocity servo loop 27 will continue to operate as before, with computer 24, coordinating its two inputs from lines 23 and 36 (through switch A) to keep the motor torque at a non-slip level. This is the calibration phase during which time the encoder output of pull roll 12 is properly equated with that of measuring wheel 9.

Identification (and resultant recalibration if required) may be initiated at timed intervals by controller 29 to keep everything in step. It is also important to provide identification just prior to the introduction of a new order.

The aspects of the invention also contemplate accelerating the downstream tail formed by severing the web at shear 4 when it is desired to adjust the transverse spacing of slitter blades 11. This acceleration is not accompanied by web-pull roll slippage, since there is no tension on the severed web tail. After acceleration, and when the leading edge of the severed upstream web portion is below cutoff knife 8, the system returns to the normal mode with motor torque at a below-slippage value.

As presently contemplated, and referring again to FIG. 3, to adjust the transverse spacing of slitter blades 11, shear 4 is fired to cut web 2 transversely, thus creating a discontinuous web with a tail portion downstream. When controller 29 receives a shear firing signal through line 32, the line tachometer 16 is disconnected from the computer input by opening of switch 28, and the controller immediately opens switch A and closes switch C. The torque signal passing through controller line 39 is arranged to be such that it will cause gradual acceleration of the pull roll and web up to the breakout point torque (100%) and beyond. Thus this torque signal includes an additional increment (X) which will be sufficient to overcome any rotational inertia of the pull roll plus accelerate it as high as desired. (See the designation at line 39 of FIG. 3: 100%+X.) When the torque signal causes pull roll 12 to reach and exceed the breakout point, there will be no slippage in this instance because of the lack of web tension, as mentioned above. The increased torque is thus translated into acceleration.

The acceleration may bring the torque up to any desired pre-set high value, until the desired size gap is formed in the now discontinuous severed web. At this point, controller (29) opens switch C and again closes switch A, with tachometer line switch 28 again being returned to closed position. The system has now returned to its condition before the shearing step.

It is contemplated that while tachometer line switch 28 is open, computer 24 takes over and feeds desired velocity information to motor 13, and thus pull roll 12.

Various types of well known sensing devices, counters, calculators, motor actuators, computers, and the interconnections therefor, can be utilized without departing from the spirit of the invention, which, in the present embodiment, provides a unique automatically operative "teaser" control for the pull roll of a web handling apparatus.

Various modes of carrying out the invention are contemplated as being within the scope of the following claims particularly pointing out and distinctly claiming the subject matter which is regarded as to the invention.

I claim:

1. In an apparatus for handling an upstream-to-downstream traveling longitudinal web of material, the combination comprising:

(a) cutoff means (8) for transversely cutting the traveling web into sheets of uniform length, (b) a pull roll (12) disposed adjacent an input to said cutoff means for feeding web into the latter, said pull roll providing a contacting interface with the web, (c) motive means (13) connected to rotatably drive said pull roll, (d) drive means (24) providing a drive signal to said motive means to drive the latter at a given torque output, (e) controller means (29) connected to said drive means for increasing the torque output of said motive means until slippage occurs at said web-pull roll interface at a breakaway torque point, with said controller means including means for identifying the value of said breakaway torque point, (f) and means associated with said controller means for decreasing the torque output of said motive means to below said identified breakaway torque point to essentially eliminate said slippage at said interface.

2. The apparatus of claim 1 which includes:

(a) shearing means (4) connected to said controller means (29) and disposed upstream of said pull roll (12) to transversely cut the traveling web so that the web is discontinuous and forms an upstream portion and a separate downstream tail portion, (b) and accelerating means associated with said controller means (29) to accelerate said motive means and said pull roll to thereby pull said tail portion downstream and away from said upstream portion of said discontinuous web to thereby form a gap therebetween.

3. In an apparatus for handling an upstream-to-downstream traveling longitudinally continuous web of material, the combination comprising:

(a) slitting means (6) for longitudinally slitting the web (2) into a plurality of side-by-side segments, (b) cutoff means (8) disposed downstream of said slitting means for subsequently transversely cutting the slit web into sheets of uniform length, (c) web position measuring means (10) disposed upstrem of said slitting means and with said measuring means being connected to actuate said cutoff means, (d) a pull roll (12) disposed adjacent an input to said cutoff means for feeding web into the latter, said pull roll providing a contacting interface with the web and having further web position measuring means **(12*a*) connected thereto, (e) motive means (13) connected to rotatably drive said pull roll, (f) drive means (24) providing a drive signal to said motive means to drive the latter at a given torque output, (g) controller means (29)** connected to said drive means for increasing the torque output of said motive means until slippage occurs at said web-pull roll interface at a breakaway torque point, and with said controller means including means for identifying the value of said breakaway torque point, (h) and means associated with said controller means for decreasing the torque output of said motive means to below said identified breakaway torque point to essentially eliminate said slippage at said interface.

4. The apparatus of claim 3 which includes: calibration means (27) for equating outputs of said first and second named web position measuring means **(10, 12*a*)**

5. the apparatus of claim 3 which includes: calibration means (27) for equating outputs of said first and second named web position measuring means **(10, 12*a*)** after said torque output of said motive means has been decreased.

6. The apparatus of claims 3, 4 or 5 which includes:

(a) shearing means (4) connected to said controller means (29) and disposed upstream of said slitting means (6) to transversely cut the traveling web so that the web is discontinuous and forms an upstream portion and a separate downstream tail portion, (b) and accelerating means associated with said controller means to accelerate said motive means and said pull roll (12) to thereby pull said tail portion downstream and away from said upstream portion of said discontinuous web to thereby form a gap therebetween for use when an adjustment is made in said slitting means.

7. The apparatus of claim 6 which includes: means associated with said controller means (29) for returning the torque output of said motive means (13) to its decreased output below said breakaway torque point after said gap has been formed.

8. A method for handling an upstream-to-downstream traveling longitudinal web of material, comprising the steps of:

(a) providing (b 1) cutoff means (8) for transversely cutting the traveling web into sheets of uniform length, (2) a pull roll (12) disposed adjacent an input to said cutoff means for feeding web into the latter so that said pull roll provides a contacting interface with the web, (3) motive means (13) connected to rotatably drive said pull roll, (4) and drive means (24) providing a drive signal to said motive means to drive the latter at a given torque output, (b) increasing the torque output of said motive means until slippage occurs at said web-pull roll interface at a breakaway torque point, (c) identifying the value of said breakaway torque point, (d) and decreasing the torque output of said motive means to below said identified breakaway torque point to essentially eliminate said slippage at said interface.

9. The method of claim 8 which includes the steps of:

(a) cutting the traveling web upstream of said pull roll (12) to transversely cut the web so that the web is discontinuous and forms an upstream portion and a separate downstream tail portion, (b) and accelerating said motive means and said pull roll to thereby pull said tail portion downstream and away from said upstream portion of said discontinuous web to thereby form a gap therebetween.

10. A method of handling an upstream-to-downstream traveling web of material, comprising the steps of:

(a) providing (1) slitting means (6) for longitudinally slitting the web (2) into a plurality of side-by-side segments, (2) cutoff means (8) disposed downstream of said slitting means for subsequently transversely cutting the slit web into sheets of uniform length, (3) web position measuring means (10) disposed upstream of said slitting means and with said measuring means being connected to actuate said cutoff means, (4) a pull roll (12) disposed adjacent an input to said cutoff means for feeding web into the latter, said pull roll providing a contacting interface with the web and having further web position measuring means **(12*a*) connected thereto, (5) motive means (13)** connected to rotatably drive said pull roll, (b) driving said motive means at a given torque output, (c) increasing the torque output of said motive means until slippage occurs at said web-pull roll interface at a breakaway torque point, (d) identifying the value of said breakaway torque point, (e) and decreasing the torque output of said motive means to below said identified breakaway torque point to essentially eliminate said slippage at said interface.

11. The method of claim 10 which includes the step of: equating outputs of said first and second named web position measuring means (10, 12*a*).

12. The method of claim 10 which includes the step of: equating outputs of said first and second named web position measuring means (10, 12*a*) after said torque output of said motive means has been decreased.

13. The method of claims 10, 11 or 12 which includes the steps of:

(a) transversely cutting the web upstream of said slitting means so that the web is discontinuous and forms an upstream portion and a separate downstream tail portion, (b) accelerating said motive means and said pull roll (12) to thereby pull said tail portion downstream and away from said upstream portion of said discontinuous web to thereby form a gap therebetween, (c) and adjusting said slitting means when said gap is disposed thereat.

14. The method of claim 13 which includes the step of: returning the torque output of said motive means (13) to its decreased output below said breakaway torque point after said gap has been formed.

* * * * *

UNITED STATES PATENT AND TRADEMARK OFFICE

CERTIFICATE OF CORRECTION

PATENT NO. : 4,809,573

DATED : March 7, 1989

INVENTOR(S) : Harold D. Welch

It is certified that error appears in the above-identified patent and that said Letters Patent is hereby corrected as shown below:

Claim 3, line 30, delete "strem" and substitute therefor --stream--.

Claim 8, line 17, delete "(b 1)" and substitute therefor --(1)--.

Signed and Sealed this

Fourteenth Day of November, 1989

*Attest:*

JEFFREY M. SAMUELS

*Attesting Officer* *Acting Commissioner of Patents and Trademarks*